United States Patent [19]

Schäfer et al.

[11] Patent Number: 5,420,042

[45] Date of Patent: May 30, 1995

[54] METHOD FOR THE ANALYTICAL DETERMINATION OF THE CONCENTRATION OF A COMPONENT OF A MEDICAL SAMPLE

[75] Inventors: Rainer Schäfer, München; Christoph Berding, Munich; Fridl Lang, Tutzing; Wilheim Kleider, Murnau; Peter Wolf, Habach, all of Germany

[73] Assignee: Boehringer Mannheim GmbH, Mannheim, Germany

[21] Appl. No.: 84,008

[22] Filed: Jun. 29, 1993

[30] Foreign Application Priority Data

Jul. 3, 1992 [DE] Germany .................. 42 21 807.1

[51] Int. Cl.⁶ .................. G01N 33/543; G01N 33/557
[52] U.S. Cl. .................. 436/517; 436/34; 436/43; 436/164; 436/518; 436/534; 436/909
[58] Field of Search .................. 436/34, 517, 518, 909, 436/43, 164, 534

[56] References Cited

U.S. PATENT DOCUMENTS 4,157,871 6/1979 Anderson et al. .............. 436/805 X
4,204,837 5/1980 Sternberg et al. .................. 436/517

FOREIGN PATENT DOCUMENTS 1236707 5/1988 Canada .
0148463 7/1985 European Pat. Off. .
2353860 12/1977 France .

Primary Examiner—David Saunders
Attorney, Agent, or Firm—Hoffmann & Baron

[57] ABSTRACT

Method for the analytical determination of the concentration of a component of a medical sample, in which a reaction of the sample with reagents leads to a time-dependent change $S(t)$ in a measured quantity $S$ and the concentration C correlates according to an evaluation curve $C(X)$ with an input variable X derived from $S(t)$, in which the calibration curve is ambiguous for at least a portion of the possible X values. In order to assign an input variable X to one of the sub-sections and thereby to obtain an unambiguous correlation to a particular concentration C, a training run and an analysis run are performed. In the training run, a discrimination algorithm is performed at least once, in which a discriminator set is generated from measurements of $S(t)$, a score is generated in each case from the latter with a multivariate statistical technique and it is checked whether the scores can be divided into separate subsets, in which the concentrations are correctly assigned to the sub-sections of the calibration curve. The discrimination algorithm is repeated with different discriminator sets generated according to different generation methods from the measurements of $S(t)$, in order to establish an operative discrimination algorithm. In the analysis run, an analysis score is calculated from measurements of $S(t)$ according to the operative discrimination algorithm, the analysis score is compared with the boundary score and the measurement result is assigned to one of the sub-curves of the calibration curve by comparison of the analysis score with the boundary score.

10 Claims, 4 Drawing Sheets

METHOD FOR THE ANALYTICAL DETERMINATION OF THE CONCENTRATION OF A COMPONENT OF A MEDICAL SAMPLE

BACKGROUND OF THE INVENTION

The invention relates to a method for the analytical determination of the concentration C of a component of a medical sample, in which a reaction of the sample with reagents leads to a time-dependent change $S(t)$ ("kinetic") in a measured quantity S and the concentration C correlates according to an evaluation curve $C=f(X)$ with an input variable X derived from $S(t)$, in which the calibration curve $X=f^{-1}(C)$ inverse to the evaluation curve $C=f(X)$ is not monotonous, so that the same value of the input variable X corresponds on at least two sub-sections of the calibration curve to different values of the concentration C, and the evaluation curve is ambiguous for at east a portion of the possible X values.

In chemical analysis, in particular with the analysis of body fluids such as blood and urine, methods are commonly used which are based on a specific binding reaction of two binding partners exhibiting biological affinity. Immunological interactions in particular are specific binding reactions in this sense, i.e. interactions between antigens or haptens on the one hand and antibodies on the other. Other examples are the lectin-sugar and biotin-streptavidin binding reactions or active substance-receptor interactions. Reference will be made below by way of example, without restricting the universality, to immunological interactions.

Methods of analysis of this kind are distinguished by high specificity and sensitivity of detection. A problem with immunological methods of analysis, which has been known for a long time, consists however in the fact that the evaluation curve $C=f(X)$ is in many cases not unambiguous. This phenomenon is also described as the "(high dose) hook effect". It is observed both with heterogeneous and with homogeneous immunological detection methods.

In the case of heterogeneous one-step sandwich tests, for example, there occurs with a high surplus of the sample antigen a saturation both of the solid-phase-bound antibody and of the labelled antibody. This results in a reduction in the coupling of the labelled antibody with the solid-phase-bound antibody and consequently a reduction in the measurement signal with rising analyte concentration.

An important example of homogeneous methods of analysis based on specific binding reactions are reactions which lead to aggregates of molecules, macromolecules or cross-linkages with small carrier particles, such as latex particles, dextrans, liposomes or metallic suspensions. Said aggregate formation leads to a change in the scattered light behaviour, which may be detected with a suitable physical method of measurement. Determination of the absorbance caused by the turbidity (turbidimetry) and measurement of the light scattering (nephelometry) are in common use.

In such tests the non-monotonous shape of the calibration curve $X=f^{-1}(C)$, which leads to the described ambiguity of the input variables X, may be explained by the fact that with high concentrations of the sample antigen the binding sites of the antibodies participating in the reaction are increasingly saturated with antigen. Consequently, with a high surplus of antigen the cross-linking of the primary particles no longer increases, but instead decreases and the turbidity diminishes.

This effect, also described as the "antigen surplus phenomenon", was recognized by Heidelberger and Kendall as long ago as 1935. The non-monotonous calibration curve is therefore often described as the "Heidelberger curve". A more detailed discussion of the problem is contained, for example, in European Patent Specification 0 148 463, to which reference is made here.

This printed publication also contains a detailed discussion of previously known methods for combating the problem of the ambiguity of the Heidelberger curves. Only a short summary of them will be given at this point.

A commonly used method is twin determination with two different sample dilutions. If the test for the diluted sample indicates an apparently higher concentration, the measured sample concentration lies in the falling part of the evaluation curve. Further dilution then usually takes place until a decreasing concentration is obtained for each of two consecutive dilutions.

Instead of the investigation of samples diluted to differing degrees, the concentration of the sample may also be varied by the subsequent addition of sample fluid. A further alternative consists in adding additional antibody after completion of an initial reaction, in order to conclude from the input variable then obtained whether the concentration to be determined lies in the rising or in the falling part of the Heidelberger curve. A disadvantage of each of said methods is that expensive additional handling stages are required. They cannot therefore be used without hesitation on normal automatic analysis units. Moreover, the additional measurement increases the measuring time and hence reduces the sample throughput of the automatic analysis unit.

Attempts are therefore often made to ensure by the use of a large quantity of antibodies that all concentrations of the analyte which occur in practice lie in the "valid measuring range", i.e. in the rising part of the Heidelberger curve. The high concentration of the antibody leads however in the range of relatively small analyte concentrations to a very flat shape of the calibration curve $X=f^{-1}(C)$ and consequently to a reduced analytical accuracy. In addition the costs of the test are increased considerably by the large quantity of antibodies. In the case of certain analytes which have to be analysed in very high concentrations or in a very wide concentration range, said method is impossible to implement in practice.

In German Patent Specification 27 24 722 an immunonephelometric method is described, which is based on the determination of the variation in time (kinetics) of the turbidity and is intended to permit without spending any more time an unambiguous assignment of the measured value to the rising or falling part of the calibration curve. In the initial period of the turbidity measurements, end point determinations had been carried out, i.e. use was made as the input variable X of the constant value of the measured quantity S which is obtained asymptotically at the end of the aggregation reaction leading to the turbidity. Some years prior to the filing date of German Patent Specification 27 24 722 it had been proposed that the long measuring time required for the end point determination be reduced by means of a kinetic measurement. Said proposal is based on the finding that the maximum rate of change of the measured quantity S ($dS/dt_{max}$), which is also referred to as $V_{max}$, may be used as the input variable X, which correlates with the concentration C of the analyte antigen with an accuracy sufficient for the quantitative analysis. Said relation C=f(X) is however also ambiguous. In German Patent Specification 27 24 722 it is proposed that the ambiguity of said evaluation curve be eliminated by means of a function of the measured quantity $V_{max}$, which is said to possess characteristically different values according to the respective surplus state. In particular the time up to the occurrence of the maximum rate of change $V_{max}$ of the turbidity signal or the derivation over time of $V_{max}$ $(dV/dt)_{max}=(d^2S/dt^2)_{max}$ is regarded as suitable for discrimination of the sub-sections of the evaluation curve. In this literature source it is noted, however, that the inherently desirable unambiguous determination of an individual concentration value is in practice not possible on this basis, because no individual time value exists at which the antibody surplus curve section lies on one side of said value and the antigen surplus curve section lies on the other side (column 21, lines 61 to 68). This problem is said to be solved by a transformation of coordinates and the introduction of new variables. If an antigen surplus state is found on this basis, the sample is diluted and the measurement repeated.

In order to overcome these disadvantages, it is proposed in European Patent Specification 0 148 463 that the functional relationship between the concentration C, the maximum rate of change of the measurement signal $V_{max}$ and the time from the start of the reaction up to the occurrence of the maximum reaction velocity $t_{max}$ be determined empirically with a standard preparation and that both $V_{max}$ and $t_{max}$ be measured from the sample, one of the two concentrations determinable from the first of said input variables being selected with the aid of the second input variable.

These known methods assume that reliable assignment to the sub-sections of the ambiguous evaluation curve C=f(X) is possible with the aid of a particular additional input variable derived from S(t). They are consequently applicable only in those cases where such a quantity may be found with sufficient discriminating potential. Moreover, these previously known methods depend on whether the curve of S(t) is determined continuously or at least at very close intervals of time (quasi-continuously). This is not possible in practice with many analytical units, because the latter, by virtue of their construction principle, permit the required turbidimetric or nephelometric measurement only at discrete measuring times with relatively large time intervals between them. This applies in particular to the commonly used analytical units which are equipped with a step-wise rotating reaction rotor, with which measurement of the contents of one of the reactors lined up at the periphery of the rotor is possible only when the latter is located at a measuring station.

OBJECTS AND SUMMARY OF THE INVENTION

On this basis the invention has as its aim the creation of a method with which the analysis is possible in the case of an ambiguous evaluation curve C=f(X) with high reliability and for a broad spectrum of different tests without additional handling steps during the sample analysis.

The aim is achieved in the case of a method of the kind described in the preamble by the fact that the following steps are carried out in order to assign an input variable X to one of the sub-sections and thereby to achieve an unambiguous correlation to a particular concentration C:

a. In a training run a discrimination algorithm is performed at least once with the following steps a.a S(t) is determined on several calibrators of known concentrations $C_j=C_l \ldots C_m$, the concentrations $C_j=C_l \ldots C_m$ lying in the two sub-sections of the calibration curve $X=f^{-1}(C)$;

a.b from the measurements of (S)t a discriminator set is generated according to a pre-determined discriminator generation method;

a.c from the discriminator set there is calculated, by a multivariate statistical technique, a score for each of the concentrations $C_j=C_l \ldots C_m$ of the calibrators;

a.d it is checked whether the scores for the concentrations $C_j=C_l \ldots C_m$ of the calibrators can be divided by means of a boundary score into separate subsets, in which the concentrations are correctly assigned to the sub-sections of the calibration curve;

b. in the training run the discrimination algorithm embracing the steps a.a to a.d is repeated with different discriminator sets generated from the measurements of s(t) by various generation methods and/or with different multivariate statistical techniques, in order to establish an operative discrimination algorithm which makes possible in the step a.d a separation of the sub-sections which is sufficiently precise for practical purposes;

c. in an analysis run:

c.a S(t) is determined from a sample to be analysed;

c.b from the latter an analysis score is calculated according to the operative discrimination algorithm;

c.c the analysis score is compared with the boundary score and c.d the input variable X and from the latter the concentration C is determined, the value X being assigned to one of the sub-curves of the calibration curve $X=f^{-1}(C)$ by comparison of the analysis score with the boundary score.

There are described as discriminator generation methods those methods by means of which, in a sequence of one or more steps, in a precisely defined manner by selection and in most cases by the additional combination of measured values $S(t_i)$ measured at particular measuring times $t_i$, numerical values are derived which are suitable for use as discriminators. In the simplest case a discriminator generation method therefore consists of only one selection step, namely the selection of a particular measured value $S(t_i)$. In most cases, however, discriminators are derived from several $S(t_i)$ values according to defined mathematical methods, which are described below also as derivation methods.

The discrimination algorithm with the steps a.a to a.d is repeated until such time as an operative discrimination algorithm is established which makes possible a separation of the sub-sections which is sufficiently precise for practical purposes. This is to be understood as meaning that a sufficiently reliable assignment, namely for the particular medical-analytical purpose, of an input variable X to one of the sub-sections of the calibration curve $X=f^{-1}(C)$ is to be possible, said assignment being achieved without additional outlay on measuring equipment, in particular without additional pipettin steps (sample dilution or increasing of the reagent concentration). A 100% correct separation, in mathematical terms, into the sub-sections is often not necessary for this purpose. Particularly in the vicinity of a maximum of the calibration curve $X=f^{-1}(C)$ it is often not relevant clinically to which of the sub-sections a measured value X is to be assigned. The maximum usually lies in the mean concentration range. Said mean concentration range corresponds to the normal values of the analyte to be determined and for this reason is less relevant in clinical terms.

It has been found, surprisingly, that according to the invention a very high reliability of the assignment to one of the sub-sections of the evaluation curve may be achieved with a small number of discrete measured values $S(t_1 \ldots t_n)$. This is particularly astonishing because in practice each of the measured values $S(t_i)$ is unavoidably affected by a statistical error rate caused in particular by the noise of the measuring arrangement. It could therefore not be anticipated that, by the selection of said measured values and with the aid of derivation methods which relate said error-affected measured values to one another, a discriminator set may be derived which permits, with the application of a multivariate statistical technique, the determination of a boundary score unambiguously separating the sub-sections. The fact that the method according to the invention itself selects the selecting discriminators and the derivation methods which lead to said discriminators, significantly contributes to this result.

BRIEF DESCRIPTION OF THE DRAWINGS

The invention will be explained in detail below with reference to the figures and the following examples, where.

DETAILED DESCRIPTION OF THE PREFERRED EMBODIMENTS

Figure 1:
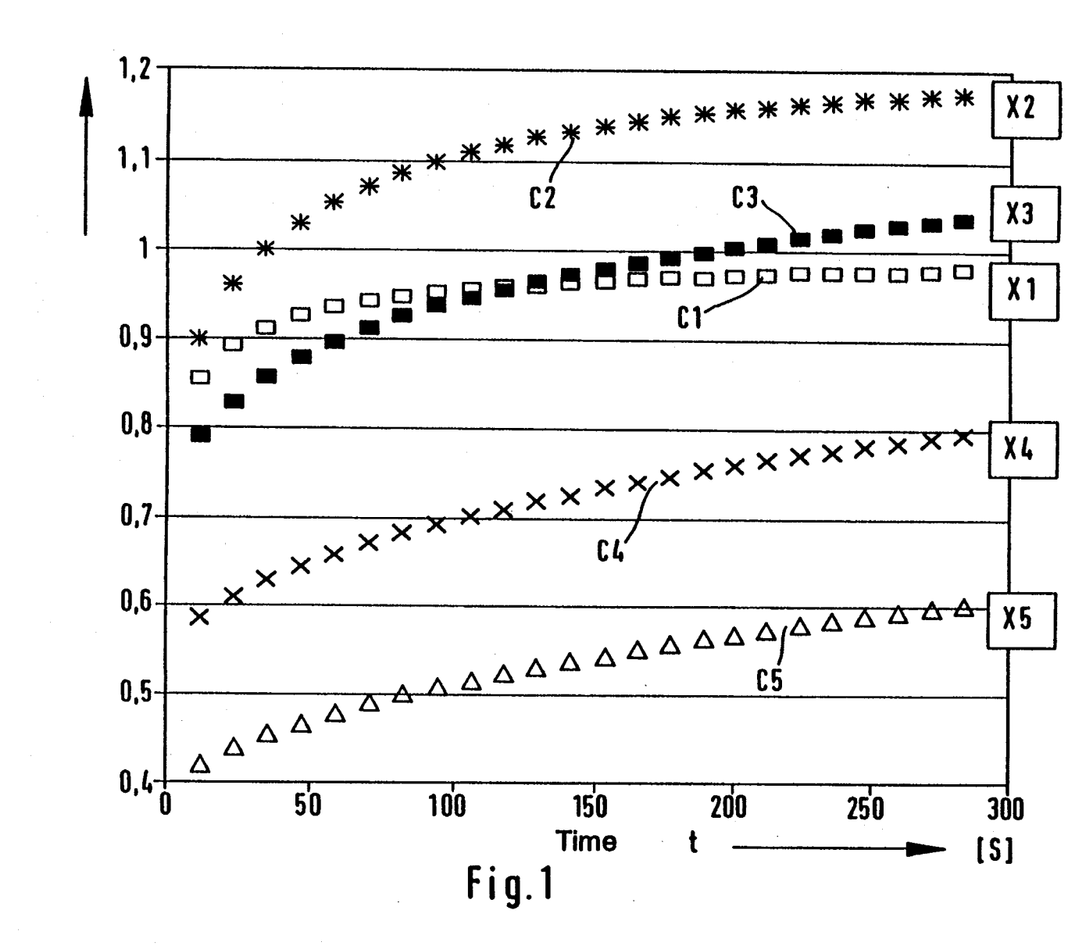
FIG. 1 shows a graph of several kinetics of absorbance S for various analyte concentrations in a turbidity test, FIG. 2 a graph of the non-monotonous calibration curve $X=f^{-1}(C)$ of an immunochemical turbidity test, FIG. 3 a graph of the distribution of the scores for an assignment based on the present invention to two sub-sections of the calibration curve $X=f^{-1}(C)$ and FIG. 4 a graph of the distribution of the scores for an assignment based on the present invention to three sub-sections of the calibration curve $X=f^{-1}(C)$.

In FIG. 1 the curve of the absorbance S is plotted in arbitrary units against the time t in seconds for five different concentrations $C_1 \ldots C_5$, where $C_1$ corresponds to the lowest and $C_5$ to the highest concentration.

For the two reaction mechanisms described in the preamble (heterogeneous one-step sandwich test, immunoturbidimetric test) and also for other test principles in which a specific binding reaction takes place which incorporates a bridge formation or linkage of two binding partners (e.g. antibodies) by means of a third, polyvalent binding partner bindable with the two other binding partners, said overall curve is characteristic. Reactions are involved which start with pre-determined proportions of the reactants (which are all constant apart from the analyte concentration) and after a rising phase pass asymptotically into a measured value plateau. The plateau value and the time plot of the reaction are determined for example in the case of the above-mentioned heterogeneous test by the number of "antigen bridge complexes", in the case of the turbidimetric test by the number of antigen-antibody cross-linkages.

Due to the fact that all factors apart from the analyte concentration are held constant, the kinetic S(t) of the measured quantity S is characteristic for the concentration C of the analyte. An input variable X is usually derived from the measured kinetic for conversion into the concentration C by means of the evaluation curve $C=f(X)$. The calibration curve $X=f^{-1}C$ is determined by means of measurements on calibrators (standard samples which contain a known concentration of the analyte) that are distributed over the whole concentration range relevant to the analysis.

In practice it is not critical for the invention in what manner the input variable X correlating with the concentration C is derived from the measured shape of the curve S(t) (i.e. the kinetics of the reaction). The concept of the input variable X embraces any quantity which can be determined from measured kinetics and correlates with the concentration C. How this happens in individual cases depends on the respective analysis and the particular features of the measuring device. With an eye to the quality of the analysis the input variable X should vary as markedly as possible as a function of the concentration. A physically interpretable quantity (such as for example the end point measurement signal which corresponds to the maximum turbidity) does not have to be involved.

It is common practice to use as the input variable X in turbidity measurements in particular, as explained, the end point or plateau value of the turbidity and the maximum rate of change $V_{max}$.

In FIG. 1 $C_1$ corresponds to the lowest, $C_5$ to the highest concentration. It will be seen that for example the end point value $X_1 \ldots X_5$ reached after approximately 300 sec. does not change monotonously with the concentration, but rises from $X_1$ to $X_2$ and then decreases up to $X_5$.

Figure 2:
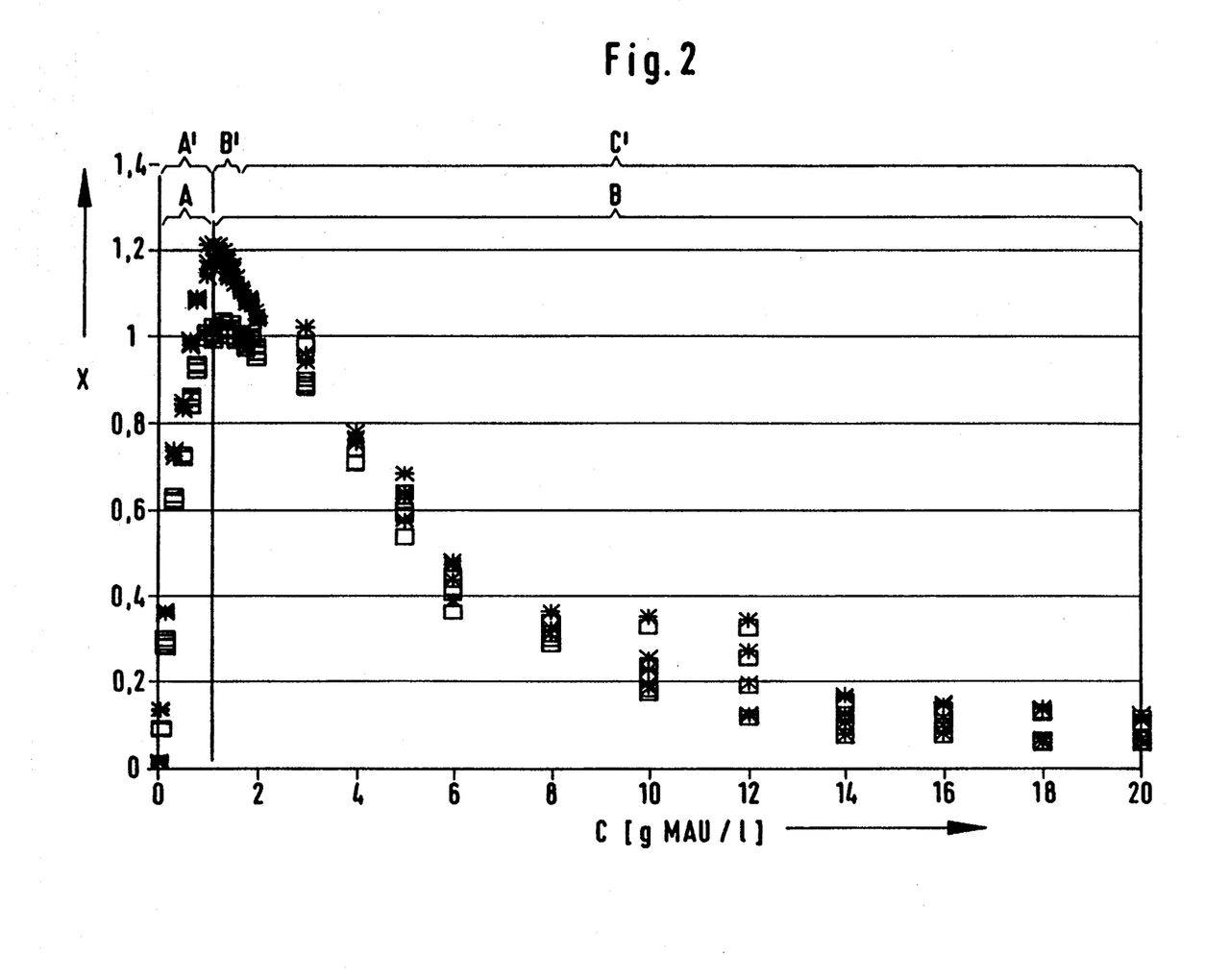

There results from this the non-monotonous shape of the calibration curve $X=f^{-1}(C)$ which is shown in FIG. 2 in the form of a Heidelberger curve. Measurement results with two different reagent batches are shown, several measurements having been carried out for each batch. The crosses here denote a first batch and the squares a second batch of the test reagents. In this way the scattering of measured values both from measurement to measurement and from batch to batch becomes clear. X is given in arbitrary units. The concentration C refers to an immunochemical test for albumin in urine ("MAU"). For example a measured value $X=0.8$ may correspond to a concentration of 0.5 or 3 g/l, depending on whether the C value lies on the rising or falling portion of the calibration curve. The evaluation curve $C=f(X)$ inverse to the curve shape shown is ambiguous. The unambiguous statement of an analytical result therefore presupposes that it is possible to assign the input variable X derived from S(t) unambiguously to one of the two sub-sections A or B of the calibration curve and thereby obtain an unambiguous correlation to a particular concentration C. To this end the following procedure is adopted according to the invention.

First of all a training run is carried out, which is used to develop, from S(t) kinetics which have been measured on calibrators, a discrimination algorithm geared specifically to the respective analysis parameter, possibly even to a particular reagent batch. The discrimination algorithm comprises a discriminator set and a multivariate statistical technique, which permits an unambiguous assignment of measured kinetics S(t) to one of the sub-sections of the calibration curve.

To this end S(t) is first of all determined on a plurality of calibrators of known concentrations, said concentrations lying in both sub-sections of the calibration curve. A comparatively small number of such calibrator measurements has proved sufficient in practice, for example six concentrations respectively on each sub-section A, B of the calibration curve. There are then obtained for example twelve kinetics of the kind shown in FIG. 1, the correct concentration C for each of the kinetics being known and it therefore also being clear to which of the sub-sections A, B of the calibration curve $X = f^{-1}(C)$ the measured kinetic is to be assigned.

From the kinetics S(t) measured there are determined, in each case according to a particular defined method which will be described as the discriminator generation method, a set of discriminators. In the context of the invention use has been made successfully as discriminators of, for example, absorbance values at particular measuring times, slopes, curvatures and roughness values. In the preferred case in which S(t) is not determined continuously, but rather at discrete measuring times $t_1 \ldots t_n$, said discriminators may for example be calculated as follows.

An absorbance value $S_i$ at a measuring point i (measuring time $t_i$) may be adopted directly. The concept of the discriminator generation method includes also, as mentioned, cases where a measured value S(t) is selected for a particular time and adopted unchanged.

A curvature $K_i$ in a measuring point i may be calculated from two individual adjacent measuring points $S_i$ and $S_{i+1}$ (measured at the times $t_i$ and $t_{i+1}$) as follows:

$$K(i) = \frac{\alpha_{i+1} - \alpha_i}{T_i} \quad (1.1)$$

$$\alpha_i = atan \frac{(S_{i+1} - S_i)}{t_{i+1} - t_i} \quad (1.2)$$

$$T_i = SQRT[(S_{i+1} - S_i)^2 + (t_{i+1} - t_i)^2] \quad (1.3)$$

SQRT here stands for square root.

The roughness is a statistical scatter parameter which has proved useful as a discriminator in particular areas of particular analyses. It is defined by $$R = \frac{1}{n} \sum_{i=j+1}^{j+n} d_i \quad (2.1)$$

$$d_i = \frac{(S_i - S_{i-1})}{S_i} \quad (2.2)$$

Numerous other discriminators, in addition to those mentioned, may also be used in the context of the invention. In each case a discriminator is for this purpose a variable derived from a measured kinetic which is established unambiguously by a defined discriminator generation method so that from a particular measured kinetic, using a particular discriminator generation method, the same value of the discriminator is obtained.

In principle other quantities, not derived from the kinetic S(t), may be used additionally as ancillary discriminators, such as for example instrument settings or measured values on environmental conditions.

Each of the discriminators is assigned to a concentration value $C_j$ and a measuring time $t_i$. The discriminator set is consequently dependent on the two independent variables C and t. Such a multi-dimensional value matrix dependent on several variables may be transferred by known multivariate statistical techniques out of the multidimensional space into a one-dimensional space. In the case of the present invention a multivariate statistical technique is used to calculate from the discriminators of a kinetic (i.e. from the discriminators which have been determined from the curve of S(t) measured on a calibrator) numerical values, so-called scores. Since it is known in which sub-section of the Heidelberger curve the respective concentration of the calibrator lies, each of the calculated scores is assigned to one of the sub-sections A or B of the Heidelberger curve.

More detailed information on methods of multivariate statistics can be obtained from the relevant literature. Reference is made for example to the following publications:

L. Fahrmeir and A. Hamerle, "Multivariate statistische Verfahren", Walter de Gruyter, New York, 1984.

SAS/STAT-User's Guide, Release 6.03, SAS-Institute Inc.

It is next checked whether the calculated scores of all the calibrators may be divided unambiguously into two subsets, so that all the scores which correspond to a concentration value in the ascending part A of the Heidelberger curve lie on one side of the boundary value (for example are smaller than said boundary value), while the scores which correspond to a concentration value on the descending sub-section B of the Heidelberger curve lie on the other side of said boundary value (i.e. are for example greater than the boundary value). A boundary value which makes such a separation possible is described as a boundary score. The boundary score is generally calculated by the same multivariate statistical technique as that by which the scores are calculated from the kinetics.

In general it is found during the above-mentioned check that it is not possible to achieve a separation adequate for practical purposes by means of a boundary score based on the initially tested discriminator set. It may be regarded as an important element of the present invention that in the training phase the operative discriminator set is determined by iteration of the above-mentioned steps. The variation of the discriminator generation methods which lead to the discriminators may moreover take place completely stochastically, i.e. the system contains a selection of discriminator generation methods which are permutated successively until the desired result (degree of separation of the scores by a boundary score which is adequate given the medical-analytical requirements) is obtained. It is naturally also possible to intervene deliberately in said training phase on the basis of pre-determined empirical values.

Overall the training run consists of a plurality of continuously repeated sections in which in each case a discrimination algorithm takes place which consists of a set of discriminator generation methods for determining the discriminators and of a defined multivariate statistical technique ,which makes possible an imaging of the multidimensional space of the discriminators on to the one-dimensionality of the scores.

It is moreover possible to vary, in addition to the discriminator generation method, also the multivariate statistical techniques used. This may also take place in principle without human intervention, there being implemented in the system various multi-variate statistical techniques which are each tested out with the same discriminator set or else with different discriminator sets in the training run. The testing of the invention has shown that it is possible to obtain in practice empirical values according to which particular multivariate statistical techniques are suitable for particular analyses. In these cases the said proven multivariate statistical technique is advisedly pre-set on the system for the determination of a particular analyte and only the discriminator generation method is varied in the training run. This is not essential, however. Circumstances are also possible in which it is advantageous to adopt a particular discriminator set and to test it in the training run in combination with different multivariate statistical techniques.

A discrimination algorithm that permits the desired separation of the scores into two subsets assigned to the sub-sections of the evaluation curve with (in the sense explained) sufficient reliability for practical purposes is described as an operative discrimination algorithm.

Depending on the requirements of the individual case, the determination of the operative discrimination algorithm may in practice be carried out either centrally by the manufacturer of the reagent kit used for the analytical determination or locally in the respective automatic analytical unit.

a) Central determination by the manufacturer has the advantage that a particularly powerful computer facility may be used. If the optimized discrimination algorithm is independent of the manufacturing batch of the reagent kit, one data transfer of the information to the analytical unit, for example by means of a diskette, is sufficient. However, if different manufacturing batches of the reagents vary to such an extent that the same optimized discrimination algorithm cannot be used for different batches, it is advisable that the optimized discrimination algorithm be determined separately for each batch and be dispatched to the clinical laboratory on a suitable storage medium with the packing of the test kit. With central determination it is not necessary to measure on the analytical unit calibrators which cover the entire relevant measuring range of the analytical determination.

b) The determination of an optimized discriminator set takes place on the unit in parallel with the determination of the calibration curve. The measurement of the kinetics S(t) does not differ in principle from normal calibration curve determinations. It is necessary, however, that the calibrators cover most of the measuring range and that a sufficient number of calibrator concentrations always lie in both sub-sections of the Heidelberger curve. In the case of units which meet said conditions, i.e. which support the determination of the complete non-linear calibration curve $X = f^{-1}(C)$, hardly any additional hardware elements or measuring equipment are required. The optimized calibration algorithm may be determined from the kinetics S(t) determined during the calibration, using the computer which is usually contained in such units.

Mixed forms consisting of the two above-mentioned variants a) and b) are naturally also possible.

In an analysis run the optimized discrimination algorithm is used as follows.

The kinetic S(t) is determined on a sample to be analysed. If the measurement takes place at discrete measuring times $t_i$, the measuring times, calculated in each case from the start of the reaction, should coincide in the analysis run with the measuring times used in the training run.

The operative discrimination algorithm is applied to the kinetics, i.e. discriminators are generated by means of the same discriminator generation methods and an analysis score is calculated from them with the aid of the same multivariate statistical technique. The assignment of the input variables X derived from the kinetic S(t) to one of the sub-sections of the calibration curve $X = f^{-1}(C)$ may then take place by simple comparison of the analysis score with the boundary score.

Among the multivariate statistical techniques, the discriminant analysis techniques are particularly preferred.

In general, discriminant analysis is used to assign objects to groups as unambiguously as possible on the basis of their p-criteria (p-dimensional criterion vectors). The group membership of each individual object has been definitively determined and is checkable. Starting from a set of objects with known group membership, in this case the kinetics, there is determined in a p-dimensional space that projection on to a one-dimensional space which produces the best possible separation of the groups.

Figure 3:
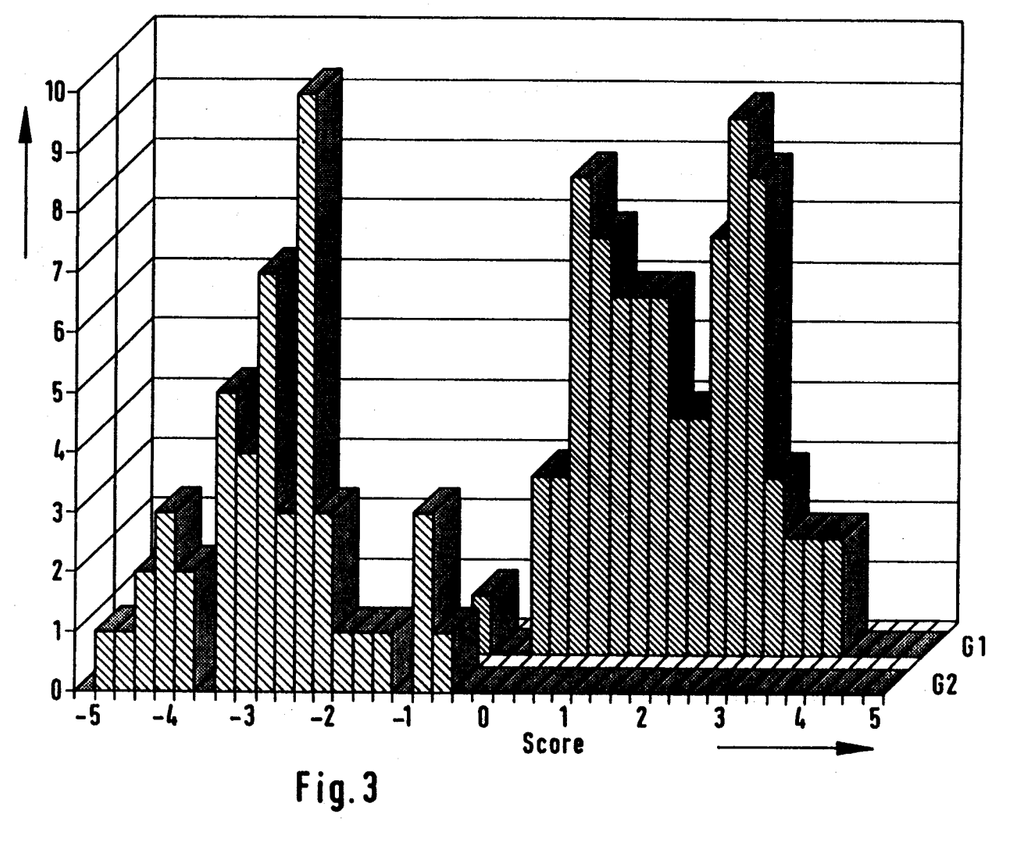

FIG. 3 shows for example a one-dimensional frequency distribution for the scores of two groups G1 and G2 of kinetics with a discrimination which is better than 95%. The discrimination of the kinetics has therefore not been 100% successful here. It is seen that a small part of the group G1 shown on the right in the figure has a score in the negative value range of the abscissa. Although the discrimination algorithm does not in this case permit a complete separation of the kinetics in mathematical terms, such a result may often be quite adequate for practical purposes if the few wrong assignments have for the reasons explained further above no practical significance for the medical-analytical result.

Successful use has been made for the discrimination in the context of the present invention of various discriminant analysis techniques. The latter are the classical linear and quadratic discriminant analysis together with nonparametric techniques, inter alia kernel estimator and nearest neighbour techniques. In the case of the kernel estimators, the kernel types uniform, normal and Epanechnikow have proved to be suitable.

The mathematical literature describes such methods in detail. Reference is made for example to the above-mentioned publications on multivariate statistical techniques and:

B. W. Silverman, Density Estimation for Statistics and Data Analysis, Chapman & Hall, London, New York, 1986.

For the estimation of the error rate the resubstitution and cross-validation methods have proved to be suitable. In the case of resubstitution the number of wrong assignments is determined for the set of kinetics in question. In the cross-validation method, the analysis is carried out with (n-1) kinetics and it is checked whether the assignment of the n-th kinetic has taken place correctly. Permutation is then carried out and after this the failure rate is determined.

EXAMPLES

Example 1

In order to determine the concentration of albumin in urine (for the diagnosis of microalbuminuria), a traditional turbidimetric turbidity test was carried out (with reagents which are obtainable commercially under the name "Tina-quant TM, Mikroalbuminurie", manufacturer: Boehriner Mannheim GmbH, Mannheim, Federal Republic of Germany). The analyses covered a concentration range of 0 to 10 000 mg MAU/1. Two different reagent batches were used, which were distinguished in particular by the manufacturing batch of the antibodies.

A Hitachi 717 TM analytical unit was used for the measurement, in which the photometric measurement takes place in a 12 second cycle, i.e. at the rate of five measurements per minute. For each sample there took place within one kinetic the first measurement after twelve seconds and thereafter further measurements at the above-mentioned measurement rate, the unit performing at each measuring point a triple measurement and using the mean measured value (median) for the further processing.

There was used as the input variable X the difference between the absorbances after 300 seconds and after 12 seconds: $X = S(300 \text{ sec}) - S(12 \text{ sec})$.

In this way there were measured in a first series of measurements with each antibody batch five samples each in twelve previously known concentrations (0;250;500;1000;1500;2000;3000;4000;5000; 6000;8000;10000 mg MAU/dl). In the second series of measurements, samples with 42 previously known concentrations (0;100;200; . . . ; 1000;1250;1500; . . . ;4750;5000;6000; . . . ;10000 mg MAU/l) were each measured three times. In the first series of measurements five X values were therefore determined for each of twelve C values and in the second series of measurements three C values for each of 42 C values, which may be represented in the manner shown in FIG. 2 as a non-monotonous Heidelberger curve.

On the basis of the measured kinetics, operative discrimination algorithms were determined in the manner described in a training run. Five curvatures were moreover determined as-discriminators for the measuring time pairs $t_1/t_2$, $t_2/t_3$, $t_3/t_4$, $t_4/t_5$ and $t_5/t_6$ (calculated in each case according to the formulas 1.1 to 1.3), together with the fifth absorbance value after the pipetting of the second reagent (i.e. start of the turbidity reaction), from which scores and a boundary score were calculated with the SAS statistics package (manufacturer: SAS Institute Inc., Cary, N.C., U.S.A.), a method of canonical discriminant analysis.

In order to check the quality of the assignment of the measured results, first of all the training run was carried out with the kinetics of Batch 1, i.e. the coefficients of the discriminatory analysis method and the boundary score were determined in a training run of the kind described. With the aid of the coefficients thus obtained, the scores of all the reaction kinetics which had been measured with the aid of Reagent batch 2 were calculated. The assignment of the respective reaction kinetics to Section A or Section B of the Heidelberger curve was determined from their relationship to the boundary score. The same procedure was repeated in reverse, the kinetics measured on Batch 2 being used for the training and the kinetics from Batch 1 then being analysed.

100% discrimination was obtained in both cases.

The same advantageous result was also obtained if selected subsets of the measurement results for both batches were used as training sets for the training run. In particular, training was carried out only with the 12 concentrations of the first series of measurements, and the 42 concentrations of the second series of measurements were correctly assigned.

Example 2

Ferritin was determined in serum samples of known concentration with the aid of a latex-reinforced (i.e., polyvalent antibody carrier) immunoturbidimetric test method ("Tina-quant TM, Ferritin", manufacturer: Boehringer Mannheim GmbH). Using two different reagent batches, 22 different concentrations were each measured in the range between 0 and 6000 ng Ferritin/ml, a six-fold determination being carried out for the one batch and a ten-fold determination for the second batch. In this case also the discriminators and a multivariate statistical technique were optimized by means of a training run of the kind described until such time as an operative discrimination algorithm was found. The following quantities, for example, proved suitable as discriminators: the second to fourth curvatures ($t_2/t_3$; $t_3/t_4$; $t_4/t_5$) and the fifth and 25th absorbances (in each case after the second reagent pipetting with a measuring rate of five measurements a minute). The chosen technique was a nonparametric discriminant technique of the above-mentioned SAS statistical program package.

Use was made as a training set for the training run in a first test, covering 22 concentrations in all, of three of the six kinetics for the training run. In a second test only 11 out of the 22 concentrations were used for the training run, selected so that they covered the whole concentration range.

All of the remaining kinetics were used as samples for the analysis run (application set). Scores were calculated with the coefficients of the DKA method determined in the training run, and the assignment of the reaction kinetics to Sections A and B of the Heidelberger curve was determined from the relationship to the boundary score. A 98% correct assignment was achieved. All of the wrong assignments were however not clinically relevant in the above sense. If only the clinically relevant wrong assignments were allowed for, a 100% correct assignment was once again achieved.

Example 3

This example corresponded experimentally to Example 1. The same discriminators and discriminant analysis techniques were used. The calibration curve was however in this case divided into three sub-sections (A',B',C' in FIG. 2), namely a first sub-section from 0 to 1.1 g MAU/ml, a second section from 1.1 to 1.5 g MAU/ml and a third sub-section from 1.5 g MAU/ml to 7 g MAU/ml. The mean concentration range was selected so that it covers a relatively small sub-section to the left and right respectively of the maximum of the Heidelberger curve.

Figure 4:
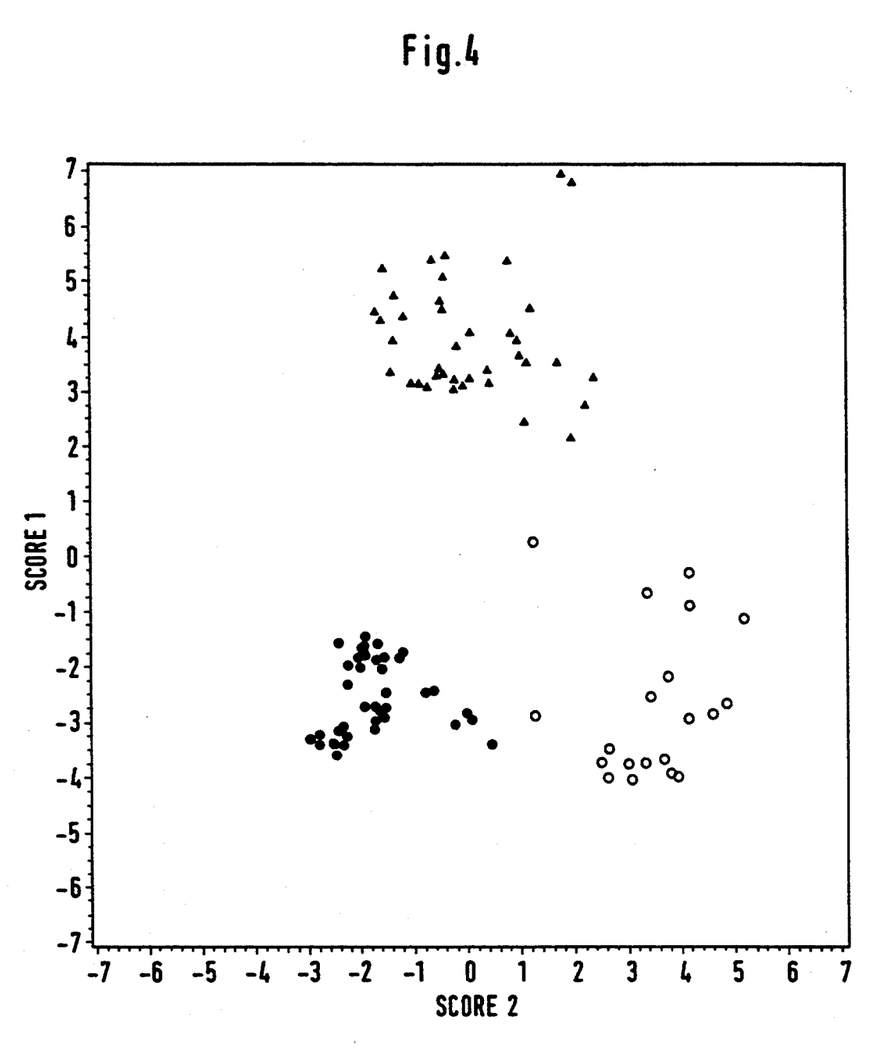

If the calibration curve is divided into more than two sub-sections, the number of boundary scores required increases. In the case of three sub-sections, two boundary scores for example are required in order to delimit the central section from each of the other two sections. In this case a canonical discriminant analysis was not used, but instead a nonparametric method with a Gauss curve as kernel function (SAS statistical program package). A 100% correct assignment of the absorbance values to the three sub-sections was achieved. FIG. 4 shows a graph of the results, in which the scores for the individual measured concentrations are plotted in two dimensions. The scores for the first concentration range A' are here shown as solid dots, the scores for the second concentration range B' as circles and the scores for the third concentration range C' as triangles.

We claim:

1. A computer-implemented method for the automated analytical determination of a concentration of a component of a medical sample by means of an automatic analytical unit, in which reacting the sample with reagents leads to a time-dependent change $S(t)$ in a measured quantity S and the concentration C correlates according to an evaluation curve $C=f(X)$ with an input variable X derived from $S(t)$, in which a calibration curve $X=f^{-1}(C)$ is not monotonous, so that the same value of the input variable X corresponds on at least two sub-sections of the calibration curve $X=f^{-1}(C)$ to different values of the concentration C and the evaluation curve $C=f(X)$ is ambiguous at least for a portion of the possible X values, wherein the method assigns the input variable X to one of the at least two sub-sections of the calibration curve $X=f^{-1}(C)$ and thereby achieves an unambiguous correlation to a particular concentration C, the method comprising the steps of:

(1) performing a training run, the training run including the steps of:
  (a) reacting with reagents a plurality of calibrator samples for which the concentrations $C_j=C_1 \ldots C_m$ are known, the concentrations $C_j=C_1 \ldots C_m$ lying in the at least two sub-sections of the calibration curve $X=f^{-1}(C)$, the step of reacting causing for each of the plurality of calibrator samples a time-dependent change $S(t)$ in a measured quantity S characteristic of each calibrator sample reacting with the reagents;
  (b) measuring the time-dependent change $S(t)$ in the measured quantity S characteristic of each calibrator sample reacting with the reagents;
  (c) generating a discriminator set from the measurements of $S(t)$ according to a pre-determined discriminator generation method;
  (d) calculating from the discriminator set a score for each of the concentrations $C_j=C_l \ldots C_m$ of the plurality of calibrator samples by a multivariate statistical technique; and
  (e) verifying whether the scores for the concentrations $C_j=C_1 \ldots C_m$ of the calibrators can be divided by means of a boundary score into separate subsets, in which the concentrations are correctly assigned to the at least two sub-sections of the calibration curve $X=f^{-1}(C)$;

(2) performing at least one additional training run, the at least one additional training run embracing the steps (1) (c) to (1) (e), wherein the generating step (1) (c) for the at least one additional training run further includes generating a different discriminator set from the measurements of $S(t)$ by at least one of a different discriminator generation method and a different multivariate statistical technique, in order to establish an operative discrimination procedure selected from all of the training runs which makes possible in step (1) (e) a separation based upon the boundary of the at least two sub-sections of the calibration curve $X=f^{-1}(C)$ and (3) performing an analysis run, the analysis run including the steps of:
  (a) reacting with reagents a medical sample for which the concentration C is unknown, the step of reacting causing a time-dependent change $S(t)$ in a measured quantity S characteristic of the reacting of the medical sample with the reagents;
  (b) measuring the time-dependent change $S(t)$ in the measured quantity S;
  (c) calculating from $S(t)$ an analysis score according to the operative discrimination procedure;
  (d) comparing the analysis score with the boundary score of the operative discrimination procedure; and
  (e) determining the concentration C from the input variable X, the input variable X being assigned to one of the at least two sub-sections of the calibration curve $X=f^{-1}(C)$ by comparison of the analysis score with the boundary score.

2. A method according to claim 1, wherein $S(t)$ is determined in steps (1) (a) and (3) (a) discontinuously at discrete measuring times $t_1 \ldots t_n$.

3. A method according to claim 2, wherein the measuring times in step (3) (a) coincide with the measuring times in step (1) (a), the measuring times being relative to the starting time of the reaction.

4. A method according to claim 2, wherein the measuring times $t_1 \ldots t_n$ have an average time interval of at least 0.5 sec.

5. A method according claim 1, wherein the discriminator set includes at least one of slope, curvature and roughness of the $S(t)$ curve at particular measuring times.

6. A method according to claim 1, wherein the multivariate statistical technique is a discriminant analysis technique.

7. A method according to claim 1, wherein the reaction includes a specific binding reaction of two binding partners exhibiting biological affinity.

8. A method according to claim 7, wherein the measured quantity S is the result of a turbidity measurement.

9. A method according to claim 8 wherein one of the binding partners exhibiting biological affinity further comprises a polyvalent antibody carrier for amplification of an immune precipitation.

10. A method according to claim 1, wherein the calibration curve is divided into more than two sub-sections (A', B', C', ...), and wherein the method further comprises the steps of performing the, training runs separately for each paired combination of the sub-sections (A', B'; A', C'; B', C'; ...), establishing in each case an operative discrimination procedure, and in the analysis run applying each of the operative discrimination procedures to each time-dependent change $S(t)$ measured according to the step (3) (a), in order to assign the measured input variables X to the sub-sections A', B', C', ...

* * * * *